United States Patent [19]

Baldeschwieler et al.

[11] 4,310,506

[45] Jan. 12, 1982

[54] MEANS OF PREPARATION AND APPLICATIONS OF LIPOSOMES CONTAINING HIGH CONCENTRATIONS OF ENTRAPPED IONIC SPECIES

[75] Inventors: John D. Baldeschwieler; Ronald C. Gamble, both of Pasadena, Calif.; Marcia R. Mauk, Vancouver, Canada

[73] Assignee: California Institute of Technology, Pasadena, Calif.

[21] Appl. No.: 123,162

[22] Filed: Feb. 20, 1980

Related U.S. Application Data

[63] Continuation-in-part of Ser. No. 13,914, Feb. 22, 1979, abandoned.

[51] Int. Cl.³ .................... A61K 49/00; A61K 43/00; B01J 13/00
[52] U.S. Cl. ........................................ 424/1; 252/316; 252/319; 424/9; 424/35
[58] Field of Search .................... 424/1, 1.5, 9, 35; 252/316, 319

[56] References Cited

U.S. PATENT DOCUMENTS

| | | | |
|---|---|---|---|
| 3,522,346 | 7/1970 | Chang | 252/316 |
| 3,663,685 | 5/1972 | Evans | 424/1 |
| 3,663,686 | 5/1972 | Grotenhuis et al. | 424/1 |
| 3,663,687 | 5/1972 | Evans | 424/1 |
| 3,683,066 | 8/1972 | Ascanio et al. | 424/1 |
| 3,932,657 | 1/1976 | Rahman | 424/319 |
| 3,937,668 | 2/1976 | Zolle | 424/1 X |
| 4,086,330 | 4/1978 | Petkau et al. | 424/1 |
| 4,089,801 | 5/1978 | Schneider | 252/316 |
| 4,115,536 | 9/1978 | Rothman et al. | 424/1 |
| 4,193,983 | 3/1980 | Ullman et al. | 424/1 X |

OTHER PUBLICATIONS

Gregoriadis, New Eng. J. Med., vol. 295, Sep. 23, 1976, pp. 704–710.

*Primary Examiner*—Christine M. Nucker
*Attorney, Agent, or Firm*—Joseph E. Mueth

[57] ABSTRACT

Unilamellar vesicles comprising a lipid bilayer, an ionophore being incorporated in said lipid bilayer, a chelating agent entrapped within the vesicles, and an effective amount of physiologically compatible cation bound to said chelating agent within the vesicles. Unilamellar vesicles are loaded by incubating the vesicles with the cation, terminating the incubation and recovering the loaded vesicles by chromatography. In some applications of the invention, the cation may be a radioactive tracer, in which case the vesicles can be administered to the human host and observed by scintillation techniques to produce a radioimage which is useful for diagnostic purposes.

32 Claims, 8 Drawing Figures

MEANS OF PREPARATION AND APPLICATIONS OF LIPOSOMES CONTAINING HIGH CONCENTRATIONS OF ENTRAPPED IONIC SPECIES

The invention described herein was made in the course of work under grants from the National Institute of Health and National Science Foundation.

BACKGROUND OF THE INVENTION

This application is a continuation-in-part of copending application Ser. No. 013,914 filed Feb. 22, 1979 on "Means of Preparation and Application of Liposomes Containing High Concentrations of Entrapped Ionic Species", now abandoned.

Lipid vesicles have been previously obtained, and observed through the use of radio-labeled liposomes, McDougall, I. R. Dunnick, J. K., McNamee, M. G., and Kriss, J. P. (1974) *Proc. Natl. Acad. Sci. U.S.A.*, 71 3487-3491; Hwang, K. J. and Mauk, M. R. (1977) *Proc. Natl. Acad. Sci. U.S.A.*, 74, 4991-4995; Hinkle, G. H., Born, G. S., Kessler, W. V., and Shaw, S. M. (1978) *J. Phar. Sci.* 67, 795-798. These vesicles contain relatively low levels of radioactive ions because of the limited amount of radioactive ions entrapped within the liposomes using simple sonication procedures. The internal aqueous volume of the vesicles is small with the result that only a few percent of the total suspension volume carrying the radioactive ions winds up inside the visicle and the balance is lost for practical purposes.

The preferred ionophore (a generic term intended to imply compounds which are ion-loving or ion attracting) [6S-[6α(2S*,3S*), 8β(R*),9β,11α]]-5-(methylamino)-2-[[3,9,11-trimethyl-8-[1-methyl-2-oxo-2-(1H-pyrrol2-yl)ethyl]-1,7-dioxaspiro[5.5]undec-2-yl]methyl]-4-benzoxazolecarboxylic acid, hereinafter referred to as ionophore A23187, has been used to complex and carry divalent cations across natural and artificial lipid membranes, Hyono, A., Hendriks, Th., Daemen, F. J. M., and Bonting, S. L. (1975) *Biochim. Biophys. Acta.*, 389, 34-46; Sarkadi, B., Szasz, I., and Gardos, G. (1976) *J. Membrane Biol.* 26, 357-370; LaBelle, E. F. and Racker, E. (1977) *J. Membrane Biol.*, 31, 301-315; Pfeiffer, D. R. Taylor, R. W. and Lardy, H. A. (1978) *Ann. N.Y. Acad. Sci.*, 307, 402-423. Evidence also exists that A23187 can form complexes with trivalent cations, e.g., $La^{+3}$, Pfeiffer, D. R., Reed, P. W., and Lardy, H. A. (1974) Biochemistry, 13, 4007-4014.

According to the present invention, we have discovered a method for routinely loading cations, which may be radioactive, into lipid visicles with greater than 90% efficiency. In this method the ionophore is incorporated in the lipid bilayer and is used to carry externally added cations to a chelator or chelating agent, which was previously entrapped in the vesicles. The binding of the cations to the chelating agent is sufficiently strong that it provides the driving force for the net transfer of the cations into the vesicles. These vescicles show more than a 100-fold increase in specific activity over those loaded by simple sonication.

Gregoriadis and coworkers have labelled liposomes with $^{111}In$ through use of $^{111}In$-labelled bleomycin, Gregoriadis, G and Neerunjun, E. D. (1975) *Biochem. Biophys. Res. Comm*, 65, 537-544; Gregoriadis, G. Neerunjun, D. E., and Hunt, R. (1977) *Life Sci.*, 21 357-369. They reported 27-80% of the added radioactivity associated with the phospholipid in negatively charged liposomes and observed 2-4.5% incorporation into positively charged liposomes.

According to this invention, we have also found that the ionophores do not interfere with the formation of the vesicles from aqueous suspension by sonication.

SUMMARY OF THE INVENTION

Briefly, the present invention comprises unilamellar vesicles comprising a lipid bilayer, an ionophore being incorporated in said lipid bilayer, a chelating agent entrapped within the vesicles, and an effective amount of physiologically compatible cation bound to said chelating agent within the vesicles.

This invention further comprehends the method comprising administering to the mammalian host unilamellar vesicles comprising a lipid bilayer, an ionophore being incorporated in said lipid bilayer, a chelating agent entrapped within the vesicles, and an effective amount of physiologically compatible radioactive tracer bound to said chelating agent within the vesicles, and observing at least some body ortion by scintillation counting technique to observe the radioimage produced.

Still further this invention includes the method of determining the distribution and condition of lipid vesicles within a mammal, said vesicles being prepared by sonication from liquid suspension or by other means and comprising a lipid bilayer, an ionophore incorporated in said lipid bilayer, a chelating agent entrapped within the vesicles, and an effective amount of physiologically compatible radioactive tracer bound to said chelating agent within the vesicles, said method comprising:

(a) determining the initial rotational correlation time of the radioactive tracer through measurement of the time-integrated perturbation factor of said vesicles, (b) injecting said vesicles into said mammal, (c) observing by scintillation techniques the distribution of said vesicles, and (d) determining any change in said time-integrated perturbation factor of the whole body or parts thereof by appropriate shielding.

In yet another aspect this invention relates to the method of loading lipid vesicles comprising:

(1) incubating unilamellar vesicles comprising a lipid bilayer, an ionophore in said lipid bilayer and a chelating agent entrapped within said vesicles, with, (2) a physiologically compatible cation, which may be a radioactive tracer, (3) terminating said incubation, and (4) recovering the loaded vesicles by chromatography.

It is an object of this invention to provide novel lipid vesicles.

More particularly, it is an object of this invention to provide novel lipid vesicles having entrapped therein increased amounts of cations, which in some applications of the invention are preferably radioactive.

These and other objects and advantages of this invention will be apparent from the detailed description which follows.

DESCRIPTION OF THE PREFERRED EMBODIMENTS

Figure 1:
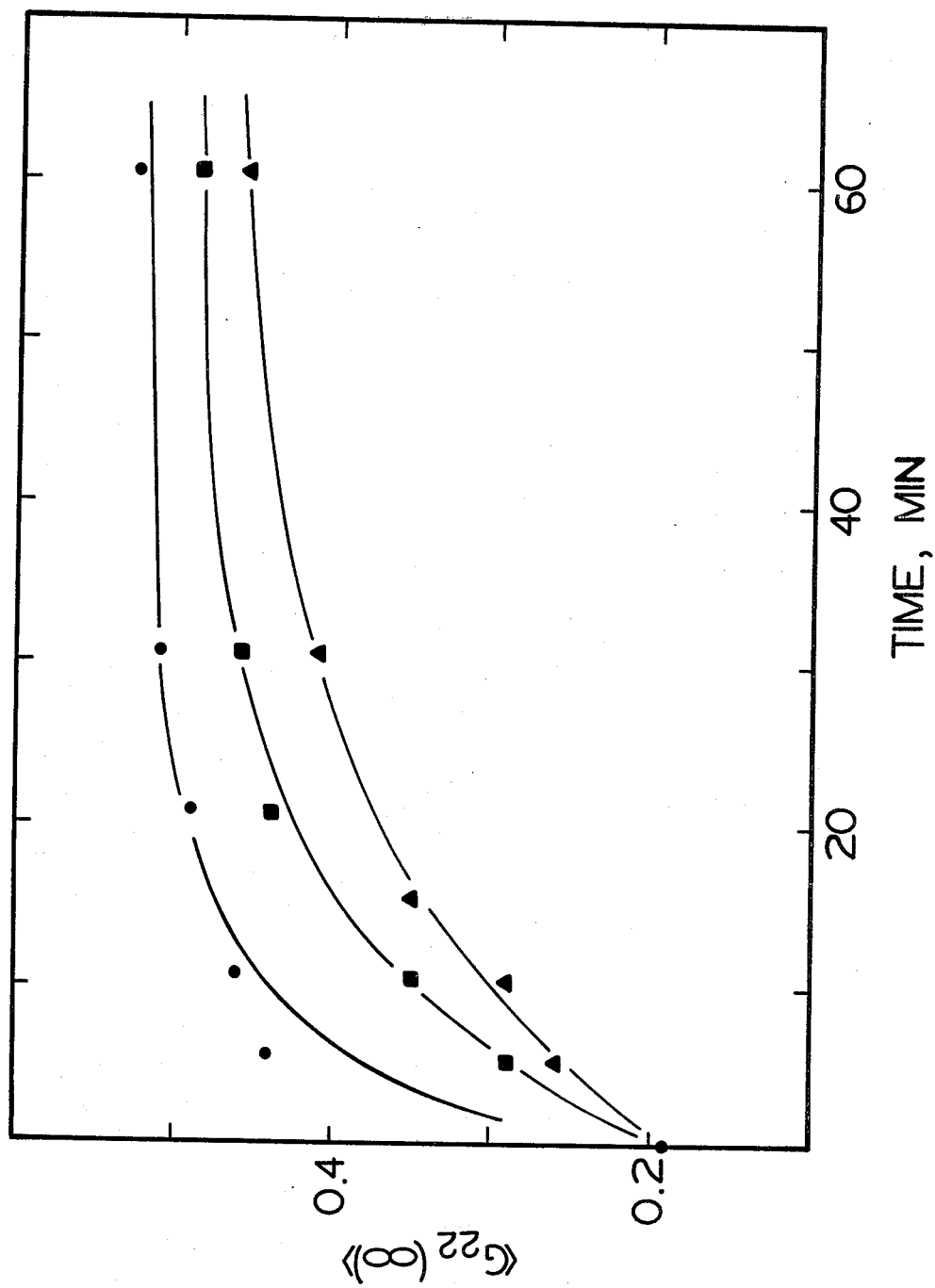

In this patent, the term "vesicles" refers to small sacs containing fluids.

Preferably the walls of the unilamellar vesicles are self-aligned layers of L-α-distearoyl phosphatidylcholine and/or L-α-dipalmitoyl phosphatidylcholine or similar lipid substances. The walls of the vehicles can also be formed from soybean phospholipid, egg yolk lecithin and L-α-dimyristoyl phosphatidylcholine. The unilamellar vesicles may be prepared by simple sonication from liquid suspension or by other techniques, such as that used in preparing the so-called Bangham's vesicles, Deamer, O., and Bangham, A. D. (1976) Biochem, Biophys Acta 443, 629-634. Bangham's vesicles, in the size range of 0.1 to 0.4 microns, are formed when ether solutions of a variety of lipids are injected into warm aqueous solutions. These vesicles are mostly unilamellar and the enclosed volume is substantially greater than the volume enclosed by sonicated vesicles.

Cholesterol, various carbohydrate analogues of cholesterol, and other additives can also be added to the phospholipid vesicle walls. For example, L-α-phosphatidyl ethanolamine, L-α-phosphatidyl-L-serine, dicetyl phosphate, and stearylamine. An ionophore is also present in the vesicle wall.

The chelator within the vesicle preferably is nitrilotriacetic acid (NTA). However, other chelators for the cations may be used. Where the cations are polyvalent metal ions, polyamino carboxylic acid chelators for such ions may be employed, such as ethylenediaminetetraacetic acid, diethylenetriaminepentaacetic acid, diaminocyclohexanetetraacetic acid and iminodiacetic acid.

In its broadest aspects, the invention contemplates that the cation or cations contained within the vesicle may be any cation which can be bound to a chelating agent. The cations are preferably selected from the group consisting of all divalent and trivalent cations. For certain applications, the cations should be radioactive tracers, desirably bivalent or trivalent, for example, $^{111}$In, $^{45}$Ca, $^{51}$Cr, $^{99}$Tc, $^{67}$Ga, $^{57}$Co, or $^{65}$Zn.

In addition to the ionophore mentioned above, ionophores generally are useful, and include polyethers: lasalocid A (X-537A), 5-bromo derivative of lasalocid; cyclic depsipeptides: beauvericin; cyclic peptides: DECYL-2 and valinomycin; and antifungal toxins: avenaciolide.

According to the present invention, the lipid vesicles can be injected into mammals by the usual administration procedures. When the cation or cations are radioactive, the flow of the vesicles within the mammals (including man) can be observed by radioimaging employing a scintillation counter to determine the location of occlusions, stenosis and the like.

The following examples are presented solely to illustrate the invention, and are not intended to be limiting in any way. In the examples, the parts and percentages are by weight unless otherwise indicated.

In the following detailed discussion, reference is made to FIGS. 1 through 8 of the drawings.

These Figures are further identified as follows:

FIG. 1, time course for loading $^{111}$In$^{3+}$ into vesicles as a function of temperature. These vesicles were composed of DSPC-cholesterol-A23187 (2:1:0.004, molar ratio). Each incubation mixture contained 5 mg lipid, 3.6 μmole citrate. $1.2\times10^{-4}$ μmole InCl$_3$ and 160 μCi $^{111}$In$^{3+}$ in 550 μl PBS. For each time point a 50 μl aliquot was removed and 50 μl calf serum was added. The triangles, squares, and circles represent the $<G_{22}(\infty)>$ values for incubations at 60°, 70°, and 80°, respectively.

Figure 2:
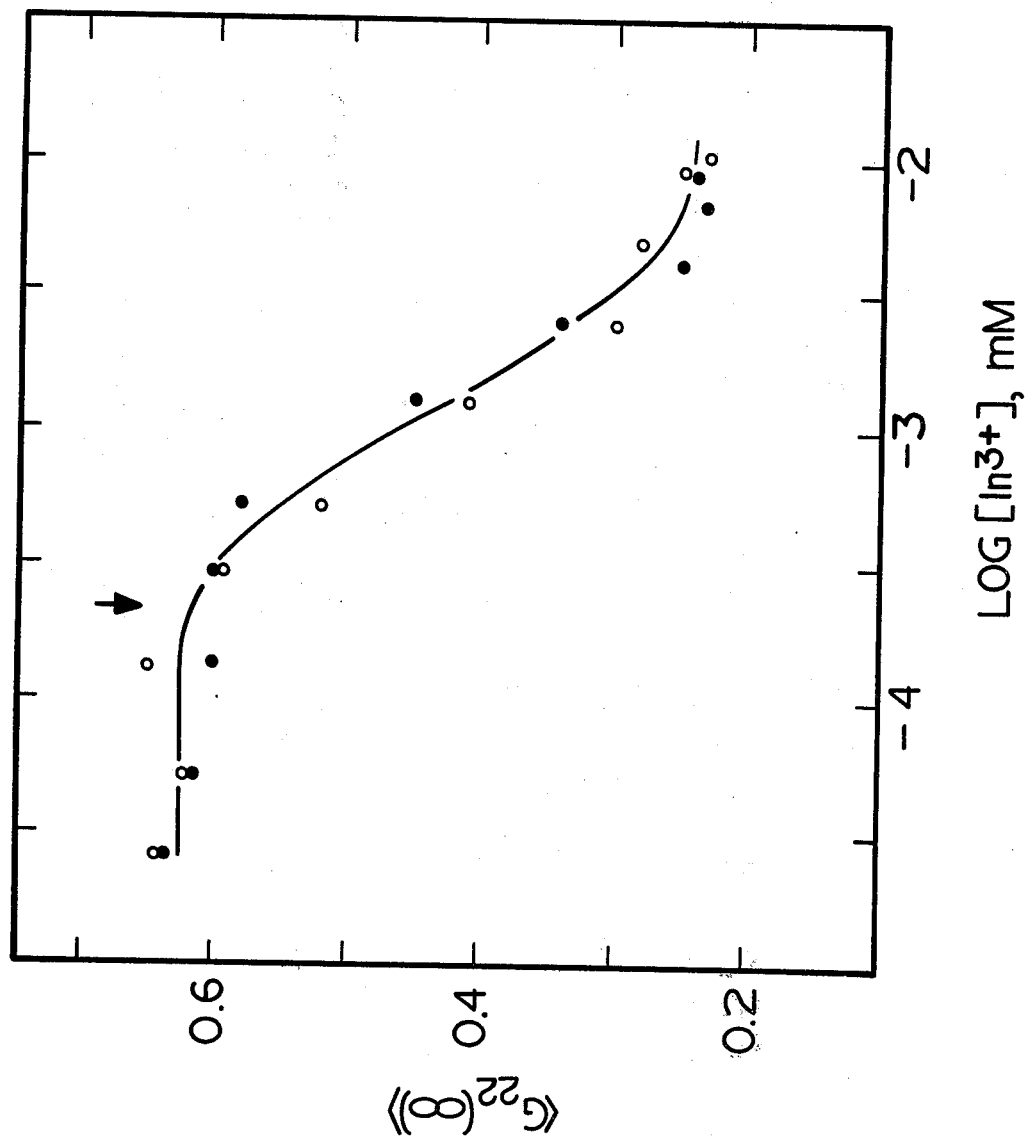

FIG. 2, dependence of vesicle loading on indium concentration. These vesicles were composed of DSPC-cholesterol-A23187 (2:1:0.004, molar ratio). Each point represents a sample containing 0.5 mg lipid, 16 μCi $^{111}$In$^{3+}$, citrate (pH 7.4) and InCl$_3$ of the indicated concentrations in a total volume of 200 μl PBS. Samples were incubated at 80° for 45 minutes. 200 μl of calf serum was then added to each sample and the $<G_{22}(\infty)>$ values measured. The open circles represent incubation in 3 mM citrate, the closed circles 6 mM citrate. The arrow indicates the indium concentration used in a standard incubation (see Example II).

Figure 3:
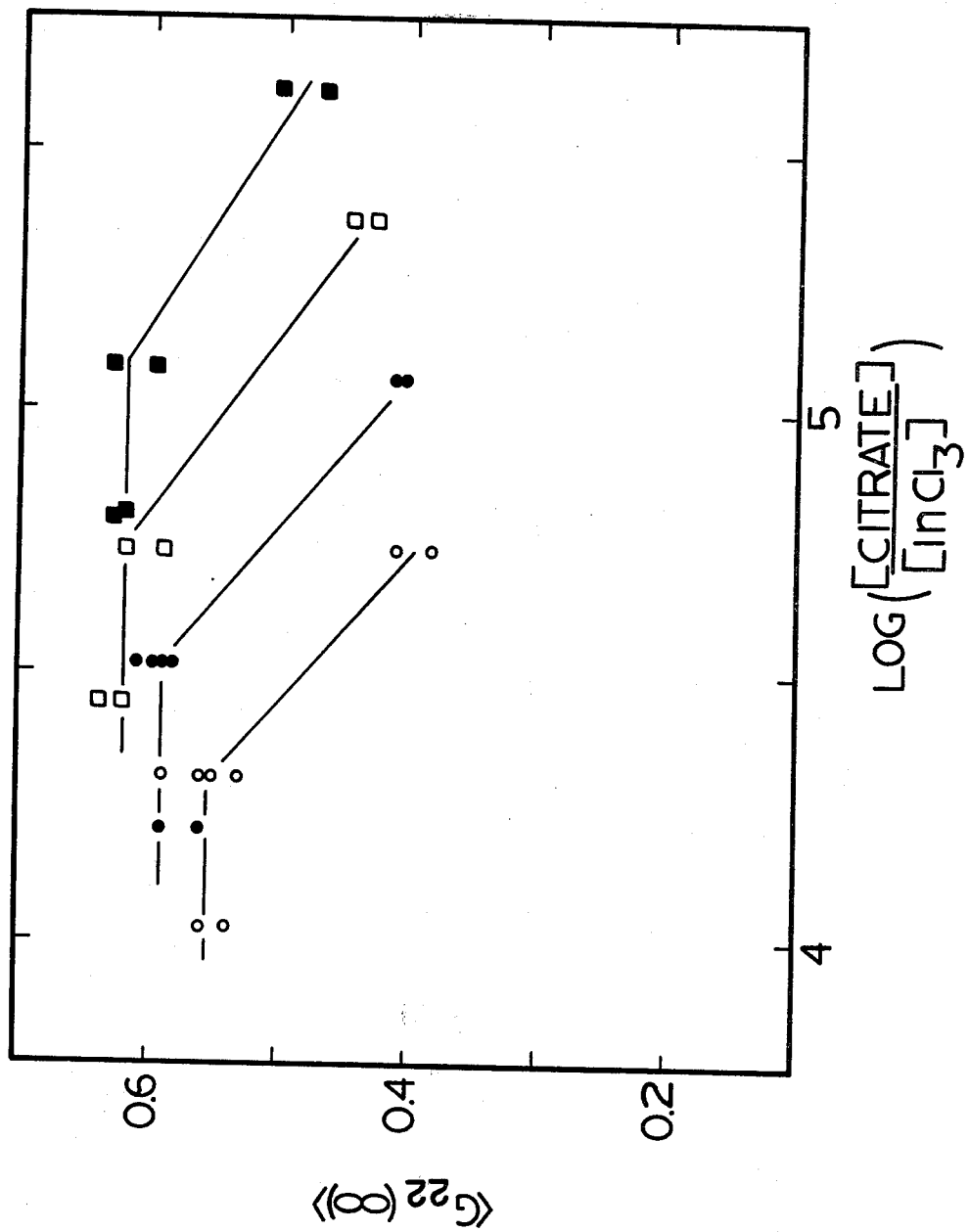

FIG. 3, vesicle loading as a function of citrate concentration. These DSPC-cholesterol-A23187 vesicles (2:1:0.004, molar ratio) were incubated and assayed under conditions specified in FIG. 2. The open circles represent $4.8\times10^{-4}$ mM In$^{3+}$, closed circles $2.4\times10^{-4}$ mM In$^{3+}$, open squares $1.2\times10^{-4}$ mM In$^{3+}$, and closed squares $4.8\times10^{-5}$ mM In$^{3+}$.

Figure 4:
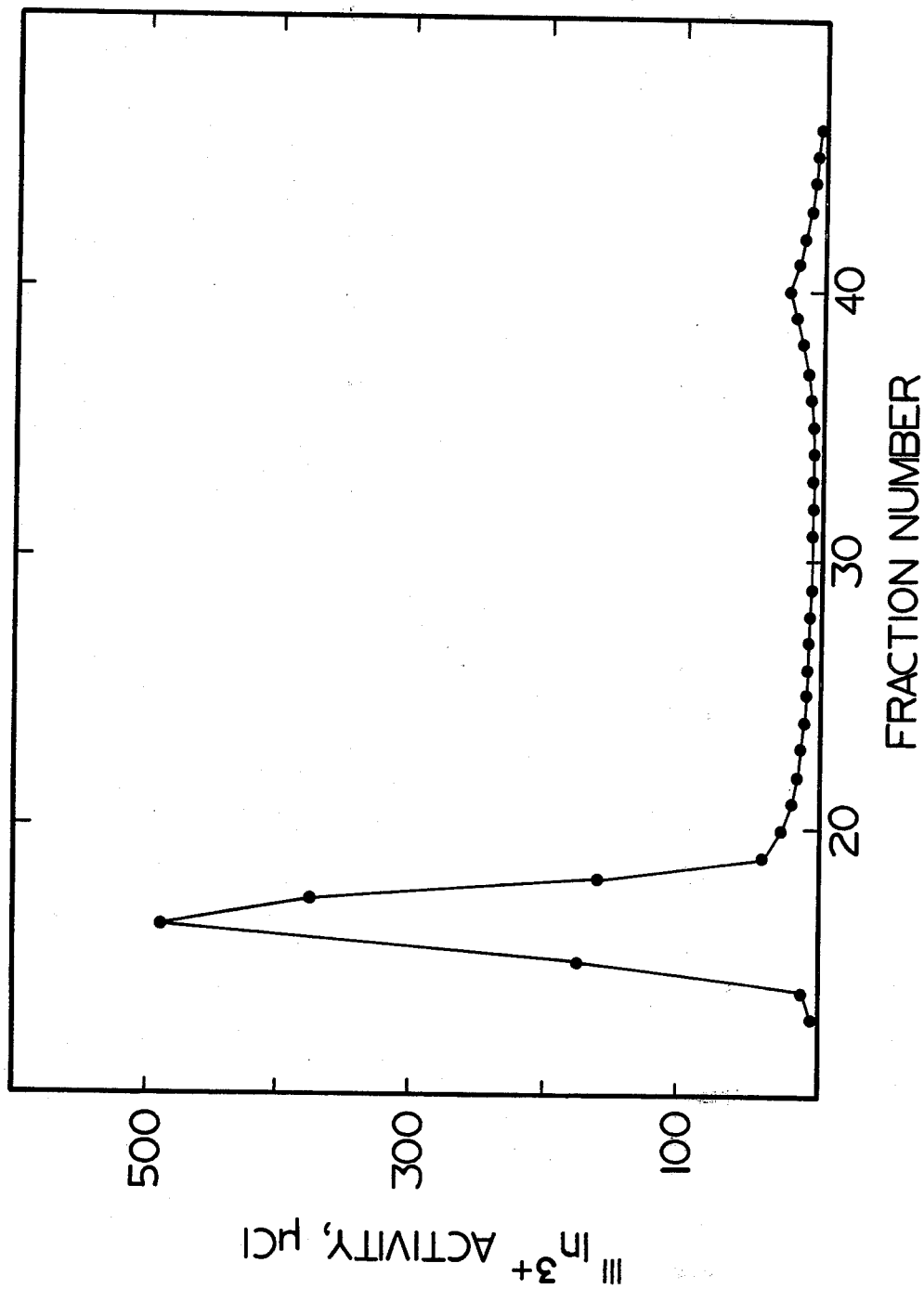

FIG. 4, the efficiency of loading of DSPC-cholesterol-A23187 vesicles (2:1:0.004, molar ratio) as assayed by Sephadex G-50 chromatography. 6.2 mg. of lipid and 1.4 mCi $^{111}$In$^{3+}$ in 0.6 ml of PBS containing $2.0\times10^{-4}$ mM InCl$_3$ and 6 mM citrate (pH 7.4) were incubated at 80° for 25 minutes. Following addition of 50 μl of 10 mM EDTA in PBS, the sample was chromatographed on a 0.8×35 cm column. Fraction size was 0.5 ml.

Figure 5:
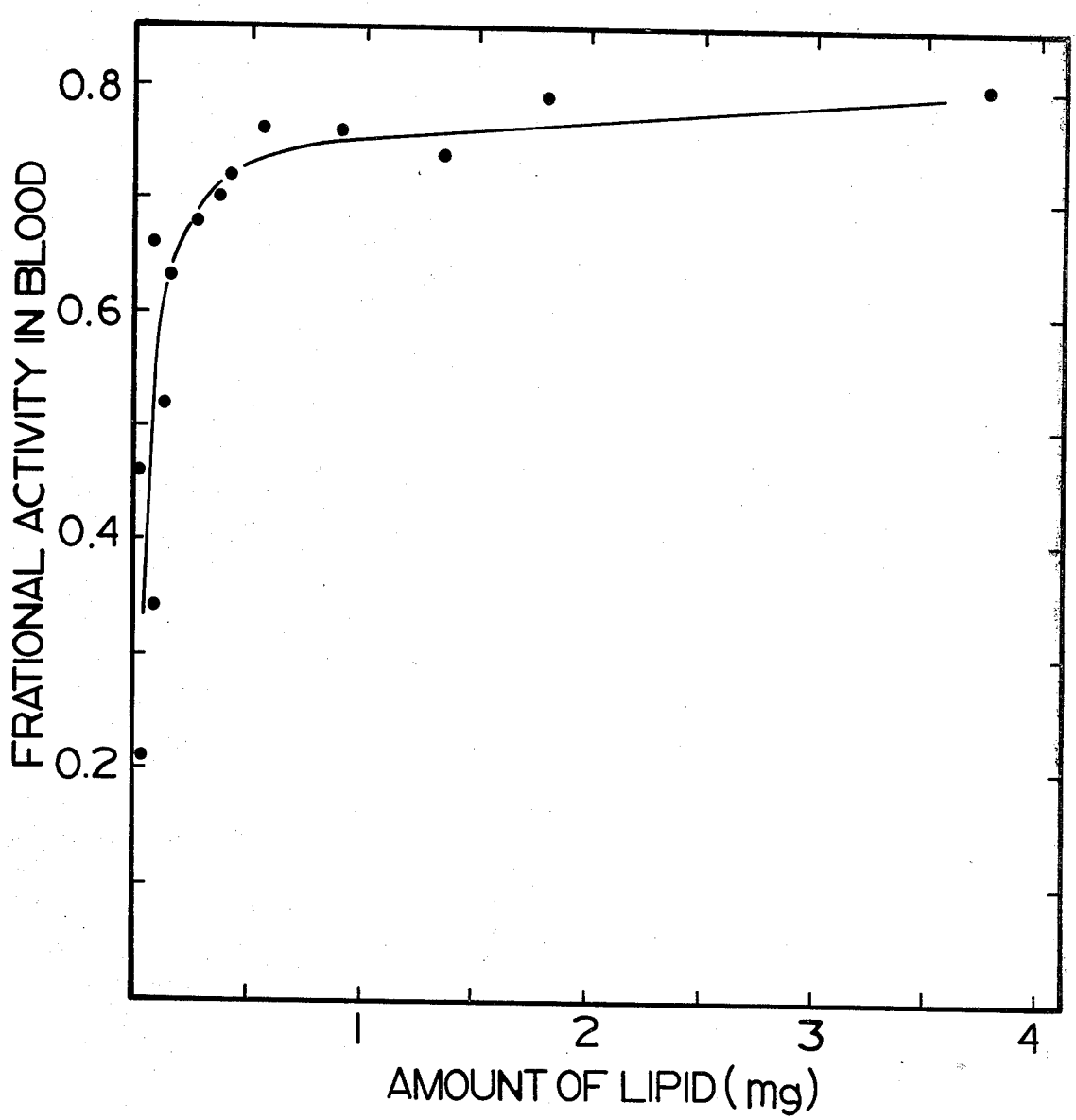

FIG. 5, saturation of liver by lipid vesicles. Mice were sacrificed 3 hours after receiving varying amounts of DSPC:Chol vesicles by intravenous injection. Each 0.40 ml injection contained ~3.0 μCi of encapsulated $^{111}$In$^{3+}$. The fractional activity in blood is defined as (total $^{111}$In$^{3+}$ in blood)/[(total $^{111}$In$^{3+}$ in blood)+(total $^{111}$In$^{3+}$ in liver)].

Figure 6:
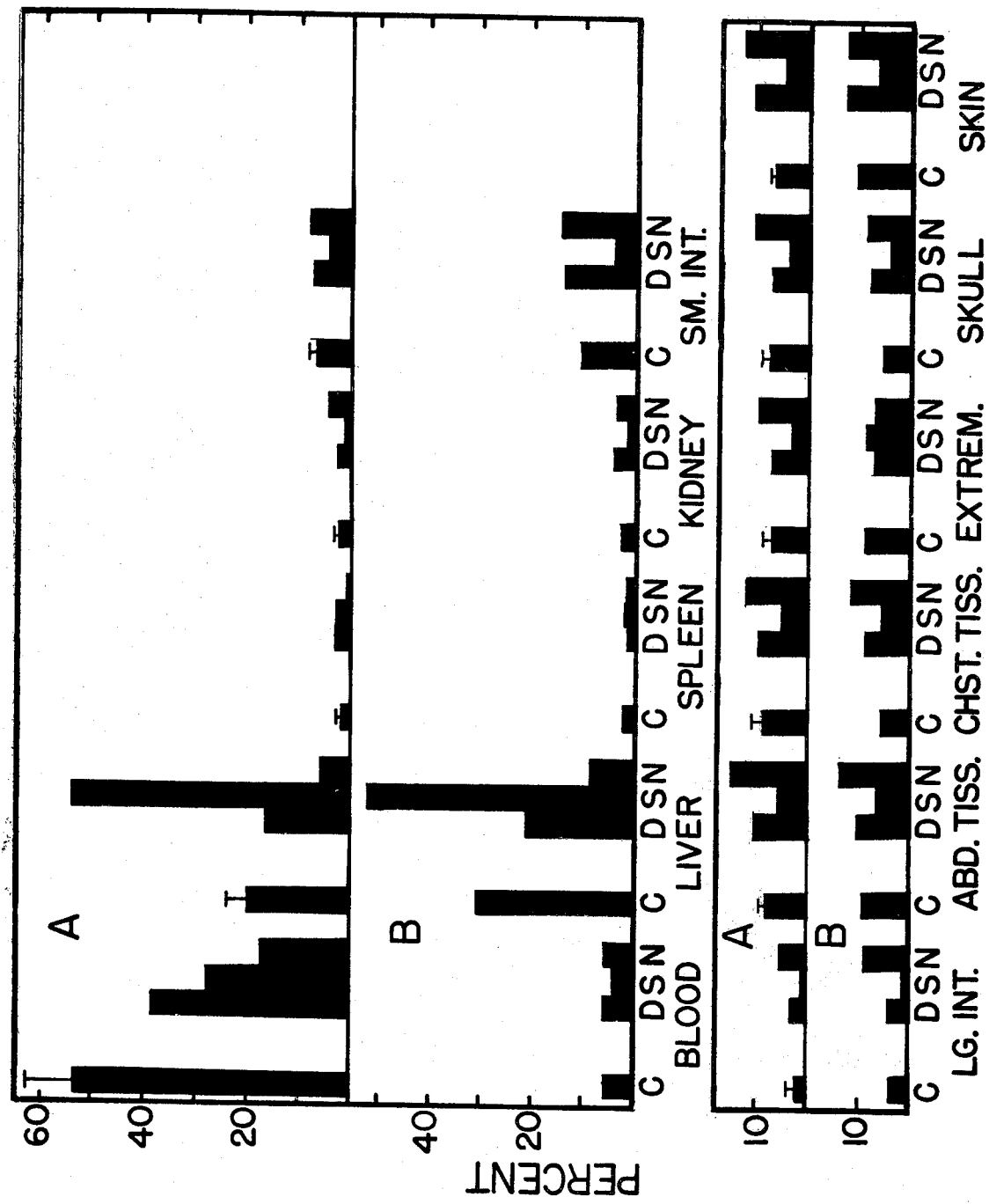

FIG. 6, tissue distribution of recovered $^{111}$In$^{3+}$ after intravenous injection of NTA-$^{111}$In$^{3+}$ or vesicles containing entrapped NTA-$^{111}$In$^{3+}$. A and B are distributions for mice sacrificed after 3 and 24 hours, respectively. Designations are C, DSPC:Chol vesicles; D,DSPC:Chol:DCP; S, DSPC:Chol:SA; and N, free NTA-$^{111}$In$^{3+}$. Each bar represents the mean of 2 to 6 mice. The error bars for C are ± S.E.M. Since no corrections were made for the blood content of various tissues, the totals can be greater than 100% when significant radioactivity is in the blood. Each 0.40 ml injection contained 1.0 mg lipid (no lipid in N) and ≧15 μCi of $^{111}$In$^{3+}$.

Figure 7:
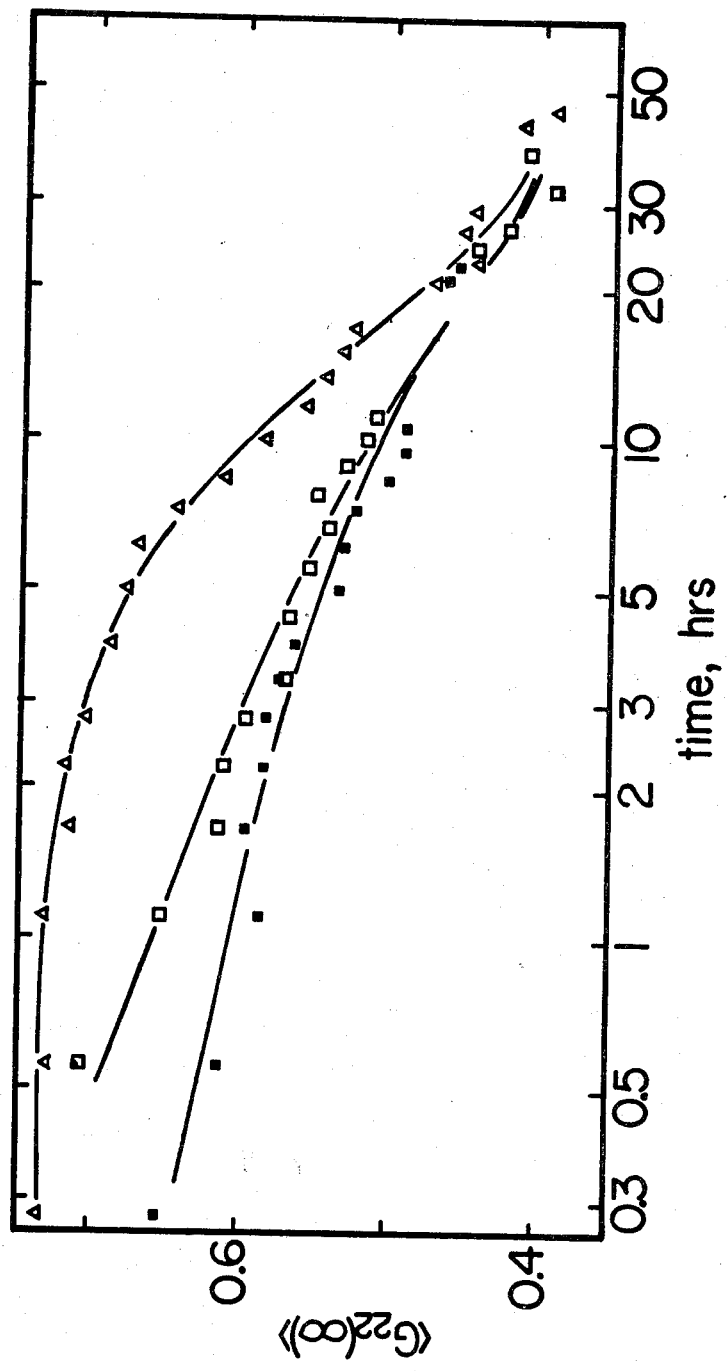

FIG. 7, stability of vesicle preparations in live mice after intravenous administration. The triangles represent DSPC:Chol vesicles, upon squares DSPC:Chol:SA, and closed squares DSPC:Chol:DCP. Each set of points is the average of two mice. Each 0.40 ml injection contained 1.0 mg lipid with 16 μCi of entrapped $^{111}$In$^{3+}$.

EXAMPLE I

Preparation of vesicles

L-α-distearoyl phosphatidylcholine (DSPC) from Calbiochem, L-α-dipalmitoyl phosphatidylcholine (DPPC) from GIBCO, and purified soybean phospholipids from Associated Concentrates, Woodside, N.Y., were used without further purification. Cholesterol was purchased from Sigma, the trisodium salt of nitrilotriacetic acid from Aldrich Chemical Co., ultrapure InCl$_3$ from Ventron Corp., and heat inactivated calf serum from GIBCO. Tritiated cholesteryl oleate [oleate-9, 10-$^3$H] was obtained from New England Nuclear. Carrier-free $^{111}$InCl$_3$ was purchased from Medi+Physics and purified. The ionophore A23187 was obtained from Eli Lilly and Co., and its preparation is described in U.S. Pat. No. 3,960,667. Unilamellar vesicles with A23187 incorporated into the bilayer were prepared using the DPPC-cholesterol and DSPC-cholesterol systems, both 2:1 (mol/mol). In a typical preparation DSPC (20 μmol), cholesterol (10 μmol) and A23187 (0.04 μmol) were dissolved in chloroform, dried to a thin film at 60° under a stream of nitrogen, and then dried in vacuo overnight. Where appropriate, 1 μCi of tritiated cholesteryl oleate (specific activity 11 μCi/μg) was included in the mixture as a marker for the lipid phase. The dried lipids were then rehydrated with 0.5 ml of 1 mM NTA in phosphate buffered saline (PBS), which is 0.9% NaCl, 5 mM sodium phosphate, pH 7.4. The mixture was sonicated in a glycerol bath which was initially at room temperature (Branson sonicator with titanium microtip, high power setting) until the solution cleared (approximately 5 minutes). Following sonication the vesicles were incubated at 60° for 10 minutes to anneal any structural defects. The vesicle suspension was then centrifuged at 300×g to remove titanium fragments and highly aggregated material. The NTA external to the liposomes was then removed by passage of the preparation over a 0.8×35 cm column of Sephadex G-50 which was equilibrated with PBS and conditioned by previous passage of lipid vesicles to saturate the irreversible binding sites. The vesicles eluted in the void volume of the column with typically a four-fold dilution and 95% recovery based on the tritiated cholesteryl oleate marker.

For several preparations the vesicle size distribution was determined by electron microscopy. The grids were prepared using vesicle suspensions diluted with PBS to concentrations not exceeding 0.1% lipid. The grids are negatively stained with 2% phosphotungstic acid.

EXAMPLE II

Loading Procedure

After Sephadex chromatography, the vesicle preparations were loaded with $^{111}In^{3+}$ using incubation mixtures consisting typically of 500 μl of vesicles, 35 μl of 3.4 μM InCl$_3$ in 104 mM sodium citrate (pH 7.4) and 1–50 μl of $^{111}In^{3+}$ in 2 mM HCl, depending on the required activity. A volume of two-fold more concentrated PBS equal to that of the $^{111}In^{3+}$ addition was included in the incubation mixture. Incubation time and temperature varied with vesicle composition as indicated below. The incubations were terminated by adding 50 μl of 10 mM EDTA (ethylenediaminetetraacetic acid) in PBS and immediately chromatographing the mixture on Sephadex G-50 equilibrated with PBS. The EDTA picks up residual indium on the outside of the vesicles so that the column does not become radioactive. In the results presented below A23187 was used to achieve loading of lipid vesicles with $^{111}In^{3+}$. The inclusion of small amounts of A23187 does not interfere with the formation of unilamellar vesicles by the sonication procedure. By electron microscopy DSPC-cholesterol-A23187 vesicles are found to have a mean diameter of 720±40 Å and are slightly larger than the DPPC-cholesterol vesicles which have a mean diameter of 650±20 Å. These preparations contained less than 10% multilamellar vesicles. The vesicles were recovered in the void volume and non-loaded $^{111}In^{3+}$, bound to EDTA, was recovered in the fractions corresponding to low molecular weight species.

Alternatively, the extent of loading was monitored by application of the gamma-ray perturbed angular correlation (PAC) technique, Leipert, T. K., Baldeschwieler, J. D., and Shirley, D. A. (1968) *Nature* 220, 907–909; Meares, C. F. and Westmoreland, D. G. (1971) *Cold Spring Harbor Symp. Quant. Biol.* 36, 511–516; Meares, C. F. Sundberg, M. W., and Baldeschwieler, J. D. (1972) Proc. Natl. Acad. Sci. U.S.A., 69, 3718–3722. A gamma-ray coincidence spectrometer is used to monitor changes in the rotational correlation time of the $^{111}In$ ion through measurement of the time-integrated perturbation factor $[<G_{22}(\infty)>]$ of solutions containing $^{111}In^{3+}$. The extent of loading was monitored by determining the $<G_{22}(\infty)>$ value of a small aliquot of the incubation mixture after the addition of an equal volume of calf serum. Any indium not entrapped in vesicles will rapidly bind to serum proteins, whereupon the $^{111}In^{3+}$ undergoes a decrease in rotational correlation time as evidenced by a decrease in the $<G_{22}(\infty)>$ value. When complete release of the entrapped $^{111}In^{3+}$ was desired, the vesicles were disrupted by the addition of 100 μl of isopropanol. All $<G_{22}(\infty)>$ values were measured at room temperature and were corrected to a standard sample size, 0.20 ml in a 10×75 mm glass tube.

Representative $<G_{22}(\infty)>$ values observed for vesicle preparations which were freed of external $^{111}In^{3+}$ are given in Table 1.

TABLE 1

Values of $<G_{22}(\infty)>$ for $^{111}In^{3+}$ in various environments[a].

| Sample | $<G_{22}(\infty)>$ without serum | with serum | with serum and isopropanol |
|---|---|---|---|
| NTA-$^{111}In^{3+}$ complex | 0.70 ± 0.02 | 0.19 ± 0.02[b,c] | 0.18 ± 0.02 |
| DPPC-cholesterol-A23187 vesicles containing NTA-$^{111}In^{3+}$ | 0.59 ± 0.02 | 0.54 ± 0.02[b] | 0.17 ± 0.02 |
| DSPC-cholesterol-A23187 vesicles containing NTA-$^{111}In^{3+}$ | 0.63 ± 0.02 | 0.62 ± 0.02[b,c] | 0.20 ± 0.02 |

[a] All samples in PBS prior to the addition of one volume of heat inactivated calf serum.
[b] Values are unchanged after 48 hours at room temperature.
[c] Values are unchanged after 48 hours at 37° C.

The inclusion of about 33 mol % cholesterol is sufficient to prevent leakage of the NTA-$^{111}In^{3+}$ complex from the vesicles in the presence of serum.

The effect of temperature on the loading of DSPC-cholesterol-A23187 vesicles is shown in FIG. 1. Maximal loading was obtained within 30 minutes at 80°. Rapid loading of soybean phospholipid-A23187 vesicles was also observed at 60°.

The amount of A23187 used in the vesicle preparations has been reduced 8-fold without a reduction in maximum loading of $^{111}In^{3+}$. However, 20-fold reduction in the amount of A23187 caused a substantial reduction (usually greater than 50%) in vesicle loading.

The presence of a suitable chelator (e.g., NTA or EDTA) in the aqueous interior was necessary for loading $^{111}In^{3+}$ into A23187 containing vesicles. The ionic character of chelating agents containing polycarboxylic acids appears to be sufficient to prevent their crossing cellular or liposomal membranes. No loading was observed with vesicle preparations entrapping only PBS or citrate in PBS.

The dependence of loading on indium and citrate concentration was also examined. Unlabeled indium chloride was added to the incubation mixtures to prevent adventitious interaction of $^{111}In^{3+}(\leq 1$ pM) with the vesicles and container walls. As shown in FIG. 2, indium concentrations above $2.5 \times 10^{-4}$ mM clearly prevent maximal loading of $^{111}In^{3+}$ into the vesicles. This decline in loading with increasing indium concentration presumably reflects the saturation of NTA contained within the vesicles. The citrate present in the incubation mixture functions as a mild chelator to reduce interactions of the indium with the phospholipid headgroups on the outer surface of the vesicles. From the data in FIG. 3, it was calculated that concentrations of citrate above 8 mM inhibited loading in all cases. Based on this information, the standard conditions chosen for large scale preparations ($2.0 \times 10^{-4}$ mM indium and 6.0 mM citrate) should yield optimal loading.

FIG. 4 is a typical elution profile for a large scale preparation of radio-labeled vesicles. In this example 92% of the added $^{111}In^{3+}$ was recovered with the vesicles. The specific activity of these vesicles was 210 $\mu$Ci/mg lipid. Loading efficiencies of 90% or greater, with specific activities of 200-300 $\mu$Ci/mg lipid, are routinely obtained under these conditions. The use of sonication procedures to load vesicles has previously yielded vesicles with specific activities of only $\sim 2$ $\mu$Ci/mg lipid. The produced described herein enables loading of neutral, positively or negatively charged, and carbohydrate containing vesicles all with 90% or greater efficiency.

According to this invention, the binding of indium to NTA is sufficiently strong relative to citrate that it provides the driving force for the net migration of indium into the vesicles. This technique is applicable to a variety of cations. In addition, preparation of radio-labeled vesicles using the ionophore A23187 is clearly favored over preparation by sonication since 90%, instead of 2-3%, of the added radioisotope is entrapped. Loading under the conditions of this invention is also preferable since adequate shielding and radioisotope containment can be easily maintained because radioisotope contact with the sonicator is eliminated. Of no less significance is the substantial additional information on in vivo vesicle behavior that should be obtainable using these vesicles which have more than a 100-fold higher specific activity.

EXAMPLE III

Preparation and Loading Vesicles with Other Compositions

Unilamellar vesicles with A23187 incorporated into the bilayer were prepared by probe sonication of lipid mixtures in a buffer solution consisting of 1 mM NTA in phosphate buffered saline (PBS), which is 0.9% Nacl, 5 mM sodium phosphate, pH 7.4. Vesicles of the following compositions were prepared: DPPC:Chol:A23187 and DSPC:Chol:A23187, both 2:1:0.004 (molar ratio); and DSPC:Chol:dicetyl phosphate (DCP):A23187 and DSPC:Chol:stearylamine (SA):A23187, both 7:2:1:0:01. Since all preparations contained A23187, reference to it will be omitted hereafter from the designated vesicle compositions. Tritiated cholesteryl oleate (1 $\mu$Ci) was included in the mixtures as a marker for the liquid phase. Following sonication, annealing, and low speed centrifugation, the NTA external to the liposomes was removed by passage of the preparation over a Sephadex G-50 column equilibrated with PBS. Determination of the lipid concentration in the fractions was based on the tritiated cholesteryl oleate marker. For several preparations the vesicle size distribution was determined by electron microscopy following negative staining with phosphotungstic acid.

Loading Procedure: The use of A23187 to facilitate loading of vesicles with $^{111}In^{3+}$ is described above and was repeated at this point.

Establishment of Standard Conditions: Measurement of $<G_{22}(\infty)>$ values for $^{111}In^{3+}$ provides an estimate of the rotational correlation time of the molecule to which the $^{111}In$ ion is bound. Values for $<G_{22}(\infty)>$ for $^{111}In^{3+}$ complex which is not encapsulated in vesicles interacts rapidly with serum and exhibits an accompanying decrease in $<G_{22}(\infty)>$. The slightly reduced values for the complex entrapped in vesicles presumably result from limited interaction of the $^{111}In^{3+}$ with the phospholipid headgroups or from some restriction of the rotational mobility of the complex when it is confined within the aqueous compartment of a vesicle. Electron microscopy indicates that the DSPC:Chol vesicles are slightly larger than the DPPC:Chol vesicles (mean diameters of 720±40 Å and 650±20 Å, respectively).

TABLE 2

$<G_{22}(\infty)>$ values for $^{111}In^{3+}$ in vesicles and various environments*

| | Without Serum | With Serum | With Serum 30 min 37° | With Serum and Isopropanol |
|---|---|---|---|---|
| NTA-$^{111}In^{3+}$ | 0.70 | 0.19 | 0.19 | 0.18 |
| DPPC:Chol | 0.59 | 0.54 | 0.43+ | 0.17 |
| DSPC:Chol | 0.63 | 0.62 | 0.62++ | 0.20 |
| DSPC:Chol:DCP | 0.61 | 0.60 | 0.59 | 0.23 |
| DSPC:Chol:SA | 0.62 | 0.62 | 0.55 | 0.21 |

*All samples in PBS prior to addition of 1 volume of heat inactivated calf serum. Error in all measurements is ±0.02.
+0.28 after 12 hours at 37°.
++Value unchanged after 48 hours at 37°.

The data in Table 2 show that both the DPPC and DSPC vesicle systems maintain their structural stability in the presence of serum at room temperature. However, at 37° serum has a very marked adverse effect on the stability of DPPC:Chol vesicles.

EXAMPLE IV

Use of vesicles in live animals

The vesicles of Example III containing $^{111}In^{3+}$ were administered to Swiss-Webster mice (18-22 g) orally or by intravenous (via tail vein), subcutaneous or intraperitoneal injection. PAC studies on live animals required $\sim 16$ $\mu$Ci $^{111}In^{3+}$ per mouse while administration of a minimum of 150 $\mu$Ci $^{111}In^{3+}$ per mouse was necessary for PAC studies on individual tissues. Radiolabeled vesicles were supplemented with unlabeled vesicles from the same preparation to adjust the total amount of administered lipid to the desired level. The volume administered orally was 75 $\mu$l while for injections the volume was maintained at 0.40 ml/mouse by the addition of PBS when necessary.

PAC studies on live animals were conducted using mice confined within the barrel of a modified plastic syringe centered in the spectrometer as described in Hwang, K. J. & Mauk, M. R. (1977) Proc. Natl. Acad. Sci. U.S.A. 74, 4991–4995; and Goodwin, G. A. Meares, C. F. and Song, C. H. (1972) Radiology 105, 669–702. The syringe was attached to a clock motor which allowed rotation of the mouse at one rpm to reduce artifacts arising as a result of inhomogeneous distribution of $^{111}In^{3+}$ within the animal. No other corrections of $<G_{22}(\infty)>$ values were made to account for the size or geometry of the mice.

PAC measurements on individual tissues were performed immediately after sacrificing the animals. At varying lengths of time the following administration of $^{111}In^{3+}$, the mice were killed by cervical dislocation followed immediately by decapitation. Organs and tissues were washed with 0.9% NaCl, blotted and weighed. PAC measurements of all tissues were completed within one hour. No change in $>G_{22}(\infty)>$ value was observed for samples remeasured within this time period. The distribution of injected radioactivity was determined by assaying the tissue samples in a well-type gamma-ray spectrometer. Distributions are reported on a per organ basis. Blood was assumed to comprise 7.3% of the total weight of the animal.

Preliminary experiments indicate substantial variability in the amount of radioactivity that was rapidly removed from the blood by the liver following administration of vesicles containing $^{111}In^{3+}$. For example, the amount of $^{111}In^{3+}$ recovered in the liver 3 hours after intravenous injection of DSCP:Chol vesicles was found to range between 18 and 80% of the injected dose. This variability is found to be dependent on the amount of administered liquid (FIG. 5). To circumvent this dose-dependent and potentially unselective uptake of vesicles by the liver, administered dosages were standardized at 1.0 mg lipid/mouse. Use of this amount, which is clearly sufficient to saturate the liver for the DSPC:Chol system and presumably for the other systems investigated, should also eliminate differences arising from minor variations in animal size.

Intravenous Administration: The tissue distribution of $^{111}In^{3+}$ was determined at various time intervals after intravenous administration of vesicles containing entrapped $^{111}In^{3+}$ (FIG. 6). The blood and liver contained most of the activity at short time points for all vesicle compositions examined. For example, with the DSPC:Chol system 10 minutes after administration, 90±14% and 11±3% of the recovered activity were found in the blood and liver, respectively (average of 4 mice). For all distributions reported, no corrections were made for the blood content of the various tissues, which accounts for the greater than 100% activity noted at short times. At long time points, e.g., 24 hours (FIG. 6), the liver was the major site of deposition of $^{111}In^{3+}$ for all vesicle systems. However, negatively charged vesicles (DSPC:Chol:DCP) showed significantly less and positively charged vesicles (DSCP:Chol:SA) significantly more $^{111}In^{3+}$ deposition in the liver than the standard system. At all time points examined, the distribution of $^{111}In^{3+}$ following administration of free NTA-$^{111}In^{3+}$ complex did not resemble that from the vesicle systems. Recoveries for all systems were usually greater than 90% of the injected dose.

The overall stability of the vehicle preparations in live animals was examined using the PAC technique (FIG. 7). During the first 30 minutes following intravenous injection only the negatively charged vesicles showed substantially reduced in vivo stability. At longer times it is clear that both charged vesicle systems show greater loss of structural integrity than the standard system.

The blood content of the individual tissues will influence the observed $<G_{22}(\infty)>$ value. This is a significant factor for highly vascular tissue such as the liver and at early time points when the $^{111}In^{3+}$ content of the blood is high. Within the limits of detection, all the $^{111}In^{3+}$ in the blood in the standard vesicle system remains encapsulated even at 24 hours after injection.

TABLE 3

$<G_{22}(\infty)>$ values of tissue following intravenous injection of vesicles containing $^{111}In^{3+}$*

|  | DSPC:Chol | | DSPC: Chol:SA | DSPC: Chol:DCP |
|---|---|---|---|---|
| HOURS | 3 | 24 | 12 | 12 |
| Blood | 0.62 | 0.61 | 0.60 | 0.52 |
| Liver | 0.43 | 0.26 | 0.23 | 0.29 |
| Spleen | 0.54 | 0.24 | 0.17 | 0.28 |
| Kidney | 0.48 | 0.24 | 0.31 | 0.28 |
| Sm. Intestine | 0.42 | 0.33 | 0.26 | 0.32 |
| Lg. Intestine | 0.24 | 0.25 | + | + |
| Abdominal Tis. | 0.49 | + | 0.25 | 0.28 |
| Chest Tissue | 0.51 | 0.29 | 0.34 | 0.34 |
| Extremities | + | + | + | + |
| Skull | 0.49 | 0.25 | + | + |
| Skin | 0.50 | 0.28 | 0.27 | 0.27 |

*The variability between duplicate samples is ≦0.03.
+Not measured.

In contrast, the $<G_{22}(\infty)>$ data for the DSPC:Chol:DCP system suggest that some vesicle destruction occurs in the circulation. This destruction is evidenced in the lower $<G_{22}(\infty)>$ values observed initially with the whole mice (FIG. 7).

Other Routes of Administration: The overall distribution and stability of the vesicle systems when administered by intraperitoneal injection approximates that observed following intravenous administration. However, considerable variability in the rate and the extent of removal of vesicles from the injection site is observed with intraperitoneal administration.

Following subcutaneous injection of radiolabelled vesicles, the $^{111}In^{3+}$ is recovered predominantly in the skin near the site of injection even 24 hours after administration. A small amount of radioactivity is found in the chest tissue which is adjacent to the injection site. The $<G_{22}(\infty)>$ values on live mice show that the vesicles remain intact for nearly 10 hours and then are rapidly degraded. Variation in the amount of vesicles administered subcutaneously (e.g., 0.1 to 1.5 mg lipid and 0.1 to 0.42 ml total volume) did not cause any substantial difference in the vesicle lifetime.

In contrast to the subcutaneous results, orally administered unilamellar vesicles are destroyed within the time necessary to complete a single PAC measurement. The tissue distribution of recovered $^{111}In^{3+}$ indicates that vesicles are not absorbed into the circulation from the gastrointestinal tract (cf. low percentage in blood and liver).

TABLE 4

| | Tissue distribution of recovered $^{111}In^{3+}$* |
|---|---|
| | Oral Administration DSPC:Chol |
| HOURS | 1 |
| Blood | 0.04 |
| Lung | 0.02 |
| Liver | 0.02 |
| Spleen | + |
| Kidney | 0.02 |
| Stomach | 4.0 |
| Small Intestine | 73 |
| Large Intestine | 20 |
| Abdominal Tissue | 0.4 |
| Chest Tissue | 0.1 |
| Extremities | 0.7 |
| Skull | 0.9 |
| Skin | 0.9 |

*Expressed as percent of total recovered radioactivity. For all systems heart ≦0.04 and brain ≦0.01.
+Below limit of detection.

The $<G_{22}(\infty)>$ values for times corresponding to those in Table 4 shows that the vesicles have broken open and the $^{111}In^{3+}$ bound to the contents of the digestive system. For example, at 1 hour for the DSPC:Chol system the $<G_{22}(\infty)>$ values for the small and large intestine were 0.27 and 0.23, respectively. The rate of vesicle destruction is not dependent on the amount of lipid administered orally over the range examined (0.1 to 1 mg). However, the rate of passage of radioactivity through the gastrointestinal tract is dependent on the feeding habits of the individual animals.

Having fully described the invention, it is intended that it be limited only by the lawful scope of the appended claims.

We claim:

1. Vesicles comprising a lipid bilayer, an ionophore being incorporated in said lipid bilayer, a chelating agent entrapped within the vesicles, and an effective amount of physiologically compatible cation bound to said chelating agent within the vesicles.

2. The vesicles of claim 1 wherein the ionophore is [6S-[6α(2S*,3S*)-,8β(R*),9β,11α]]-5-(methylamino)-2-[[3,9,11-trimethyl-8-[1-methyl-2-oxo-2-(1H-pyrrol-2-yl)ethyl]-1,7-dioxaspiro[5,5]undec-2-yl]methyl]-4-benzoxazolecarboxylic acid.

3. The vesicles of claim 1 wherein the cation is selected from the group consisting of all bivalent and trivalent cations.

4. The vesicles of claim 1 wherein the cation is a radioactive tracer.

5. The vesicles of claim 1 wherein the cation is a radioactive tracer selected from the group consisting of: $^{111}$In, $^{45}$Ca, $^{51}$Cr, $^{99}$Tc, $^{67}$Ga, $^{57}$Co, and $^{65}$Zn.

6. The vesicles of claim 1 wherein the bilayer includes cholesterol.

7. The vesicles of claim 1 wherein the bilayer includes L-α-distearoyl phosphatidylcholine (DSPC).

8. The vesicles of claim 1 wherein the bilayer includes L-α-dipalmitoyl phosphatidylcholine (DPPC).

9. The vesicles of claim 1 wherein the chelating agent is selected from the group consisting of nitrilotriacetic acid, diethylenetriaminepentaacetic acid, diaminocyclohexanetetraacetic acid, iminodiacetic acid and ethylenediaminetetraacetic acid.

10. The method comprising administering to the mammalian host vesicles comprising a lipid bilayer, an ionophore being incorporated in said lipid bilayer, a chelating agent entrapped within the vesicles, and an effective amount of physiologically compatible radioactive tracer bound to said chelating agent within the vesicles, and observing at least some body portion by scintillation counting technique to observe the radioimage produced.

11. The method of claim 8 wherein the ionophore is [6S-[6α(2S*,3S*),8β(R*),9β,11α]]-5-(methylamino)-2-[[3,9,11-trimethyl-8-[1-methyl-2-oxo-2-(1H-pyrrol-2-yl)ethyl]-1,7-dioxaspiro[5,5]undec-2-yl]methyl]-4-benzoxazolecarboxylic acid.

12. The method of claim 10 wherein the tracer is selected from the group consisting of: $^{111}$In, $^{45}$Ca, $^{51}$Cr, $^{99}$Tc, $^{67}$Ga, $^{57}$Co, and $^{65}$Zn.

13. The method of claim 10 wherein the bilayer includes cholesterol.

14. The method of claim 10 wherein the bilayer includes L-α-distearoyl phosphatidylcholine (DSPC).

15. The method of claim 10 wherein the bilayer includes L-α-dipalmitoyl phosphatidylcholine (DPPC).

16. The method of claim 10 wherein the chelating agent is selected from the group consisting of nitrilotriacetic acid, diethylenetriaminepentaacetic acid, diaminocyclohexanetetraacetic acid, iminodiacetic acid, and ethylenediaminetetraacetic acid.

17. The method of determining the distribution and condition of vesicles within a mammal, said vesicles comprising a lipid bilayer, an ionophore being incorporated in said lipid bilayer, a chelating agent entrapped within the vesicles, and an effective amount of physiologically compatible radioactive tracer bound to said chelating agent within the vesicles, said method comprising:

(a) determining the initial rotational correlation time of the radioactive tracer through measurement of the time-integrated perturbation factor of said vesicles, (b) injecting said vesicles into said mammal, (c) observing by scintillation techniques the distribution of said vesicles, and (d) determining any change in said time-integrated perturbation factor of the whole body or of parts by appropriate shielding.

18. The method of claim 17 wherein the ionophore is [6S-[6α(2S*,3S*),8β(R*),9β,11α]]-5-(methylamino)-2-[[3,9,11-trimethyl-8-[1-methyl-2-oxo-2-(1H-pyrrol-2-yl)ethyl-1,7-dioxaspiro[5,5]undec-2-yl]methyl]-4-benzoxazolecarboxylic acid.

19. The method of claim 17 wherein the tracer is selected from the group consisting of: $^{111}$In, $^{45}$Ca, $^{51}$Cr, $^{99}$Tc, $^{67}$Ga, $^{57}$CO, and $^{65}$Zn.

20. The method of claim 17 wherein the bilayer includes cholesterol.

21. The method of claim 17 wherein the bilayer includes L-α-distearoyl phosphatidylcholine (DSPC).

22. The method of claim 17 wherein the bilayer includes L-α-dipalmitoyl phosphatidylcholine (DPPC).

23. The method of claim 17 wherein the chelating agent is selected from the group consisting of nitrilotriacetic acid, diethylenetriaminepentaacetic acid, diaminocyclohexanetetraacetic acid, iminodiacetic acid, and ethylenediaminetetraacetic acid.

24. The method of loading lipid vesicles comprising:

(1) incubating vesicles comprising a lipid bilayer, an ionophore in said lipid bilayer and a chelating agent entrapped within said vesicles, with, (2) a physiologically compatible cation, (3) terminating said incubation, and (4) recovering the loaded vesicles by chromatography.

25. The method of claim 24 wherein the ionophore is [6S-[6α(2S*,3S*),8β(R*),9β,11α]]-5-(methylamino)-2-[[3,9,11-trimethyl-8-[1-methyl-2-oxo-2-(1H-pyrrol-2-yl)ethyl]-1,7-dioxaspiro[5,5]undec-2-yl]methyl]-4-benzoxazolecarboxylic acid.

26. The method of claim 24, wherein the cation is selected from the group consisting of all bivalent and trivalent cations.

27. The method of claim 24, wherein the cation is a radioactive tracer.

28. The method of claim 24 wherein the cation is a radioactive tracer selected from the group consisting of: $^{111}$In, $^{45}$Ca, $^{51}$Cr, $^{99}$Tc, $^{67}$Ga, $^{57}$Co, and $^{65}$Zn.

29. The method of claim 24 wherein the bilayer includes cholesterol.

30. The method of claim 24 wherein the bilayer includes L-α-distearoyl phosphatidylcholine (DSPC).

31. The method of claim 24 wherein the bilayer includes L-α-dipalmitoyl phosphatidylcholine (DPPC).

32. The method of claim 24 wherein the chelating agent is selected from the group consisting of nitrilotriacetic acid, diethylenetriaminepentaacetic acid, diaminocyclohexanetetraacetic acid, iminodiacetic acid, and ethylenediaminetetraacetic acid.

* * * * *